United States Patent [19]

Cairns et al.

[11] 4,409,237

[45] Oct. 11, 1983

[54] PHARMACEUTICAL COMPOSITIONS CONTAINING SODIUM CHROMOGLYCATE AND β2 SELECTIVE BRONCHODILATORS

[75] Inventors: Hugh Cairns; Peter M. Greenhalgh, both of Loughborough; Brian Howlett, Leicester, all of England

[73] Assignee: Fisons Limited, Ipswich, England

[21] Appl. No.: 256,021

[22] Filed: Apr. 21, 1981

[30] Foreign Application Priority Data

Apr. 30, 1980 [GB] United Kingdom ................. 8014197
Feb. 19, 1981 [GB] United Kingdom ................. 8105306

[51] Int. Cl.³ ............................................. A61K 31/35
[52] U.S. Cl. ..................................... 424/283; 424/330
[58] Field of Search ........................................ 424/283

[56] References Cited

PUBLICATIONS

Merck Index–9th ed., 1976, paragraphs 206, 3908, 5079 & 8879.
Goodman & Gilman–The Pharmacological Basis of Therapeutics, 6th ed., 1980, pp. 166, 167 & 168.
Chemical Abstracts 82:175230v–82:175231w (1975).

Primary Examiner—Leonard Schenkman
Attorney, Agent, or Firm—Merriam, Marshall & Bicknell

[57] ABSTRACT

There are described salts of 1,3-bis(2-carboxychromon-5-yloxy)propan-2-ol with certain long acting or β2 selective bronchodilators.

There are also described certain pharmaceutical mixtures comprising
 (a) one or more of 1,3-bis(2-carboxychromon-5-yloxy)-propan-2-ol, or a pharmaceutically acceptable salt thereof, in combination with
 (b) one or more β2 selective or long acting bronchodilators, or a pharmaceutically acceptable salt thereof.

12 Claims, No Drawings

PHARMACEUTICAL COMPOSITIONS CONTAINING SODIUM CHROMOGLYCATE AND β2 SELECTIVE BRONCHODILATORS

This invention relates to new compounds, mixtures and methods for their preparation and use.

A variety of bronchodilators have been known for many years for use in the palliative treatment of allergic conditions of the lung. These bronchodilators have, in many cases been administered systemically, e.g. as elixirs, tablets, capsules, injections etc, all of which dosage forms are susceptible to overdosage. Furthermore most of the bronchodilators have unwanted side effects, e.g. on the cardiovascular system. Moreover the bronchodilators are, in general, used to treat an asthmatic attack which has already started, i.e. they are not used prophylactically.

Sodium cromoglycate has also been recommended for use in the treatment of allergic and other conditions, and in particular of asthma and rhinitis. By way of contrast to the bronchodilators sodium cromoglycate has no smooth muscle relaxant activity, but has been used prophylactically, i.e. to prevent the onset of an attack of these diseases. Thus sodium cromoglycate has not in general been recommended for use in a curative sense, i.e. for symptomatic relief during an attack of the allergy. Furthermore sodium cromoglycate has, in contrast to the bronchodilators, only been administered by inhalation for the treatment of asthma.

Sodium cromoglycate has in the past been sold as a dry powder formulation, which on inhalation has, in some patients, caused some minor bronchoconstriction. In order to overcome this minor bronchoconstriction, a formulation of sodium cromoglycate with a sub-therapeutic dose of the rapidly, but briefly acting and non-β2 selective bronchodilator isoprenaline sulphate has been sold for use in particularly broncho-responsive patients. The present concept of incorporatiang a full therapeutic dose of a long acting or β2 selective bronchodilator owes nothing to the prior incorporation of a low, non-therapeutic dose of isoprenaline sulphate in sodium cromoglycate formulations.

It is well known that patients generally dislike and are erratic in taking medicines and that when they have two separate medicaments to take they tend to omit to take one of them, or, inappropriately, take more of one than of the other.

We have now found that mixtures of sodium cromoglycate with a specific group of β2 selective bronchodilators, salts of 1,3-bis(2-carboxychromon-5-yl-oxy)propan-2-ol with those bronchodilators, and mixtures of these salts with sodium cromoglycate or the β2 bronchodilator at the appropriate therapeutic ratio, possess the advantage that they are both palliative and prophylactic, are more effective, produce less side effects, can be used at lower doses, can be administered directly to the site of the allergy, e.g. by inhalation, are longer acting, are more stable, are synergistic, cause better patient compliance or possess other desirable properties as compared to certain bronchodilators when used on their own, sodium cromoglycate when used on its own, or certain other mixtures when tested in relevant pharmacological models.

From the mode of action of sodium cromoglycate, and of the bronchodilators one would expect less than additive effects. Thus the sodium cromoglycate prevents the release of the mediators of anaphylaxis, and it is only in so far as the sodium cromoglycate is ineffective that the bronchodilator can have a useful effect.

The mixtures and salts of the present invention enable the patient to use a single medication to obtain both prophylactic and symptomatic treatment, and also enable both medicaments to be administered with less excipients (usually about half the quantity) necessary to administer the two medicaments separately. The reduction of the quantity of excipients administered is particularly advantageous as certain excipients, e.g. aerosol propellants may be damaging to the health of patients, especially atopic patients.

According to the invention we provide a salt of 1,3-bis(2-carboxychromon-5-yloxy)propan-2-ol with a long acting or β2 selective bronchodilator, provided that the bronchodilator is not of formula I,

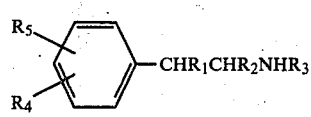

in which $R_1$ is hydrogen or —OH, $R_2$ is hydrogen, methyl or ethyl, $R_3$ is hydrogen or lower, e.g. C 1 to 6, alkyl, and $R_4$ and $R_5$, which may be the same or different, each represent hydroxy, methoxy or hydroxymethyl.

By the term a β2 selective bronchodilator we mean a beta adrenoceptor agonist which has a greater affinity for β2 adrenoceptors, stimulation of which results in relaxation of bronchial (and also arterial and uterine) muscle, than for β1 adrenoceptors, agonists of which produce cardiac stimulation (and lipolysis). For the determination of β2 selectivity, a comparison is made of the activity of the compound, (a) as a relaxant of isolated guinea-pig tracheal preparations with spontaneous tone ($EC_{50}$=molar concentration giving 50% of maximum relaxation response to isoprenaline), and (b) in increasing atrial beat frequency of isolated spontaneously beating atria from guinea-pig hearts ($EC_{50}$=molar concentration causing 50% of maximum increase in rate induced by isoprenaline). A β2 selective compound will have a lower $EC_{50}$ on the trachea than on the atria. A selectivity ratio can be determined which is the antilog of the difference between the negative log $EC_{50}$ (trachea) and negative log $EC_{50}$ (atria). The greater this selectivity ratio, the more selective is the compound for β2 adrenoceptors.

By the term 'long acting' we mean that the compound has a longer duration of action as a relaxant of bronchial smooth muscle in pharmacological tests than does isoprenaline or orciprenaline. For duration of action studies, a comparison is made of the effect of equiactive i.v. doses of compounds as inhibitors of acetylcholine—or histamine-induced bronchospasm in anaesthetized guinea-pigs. The duration of action of isoprenaline in such a test is relatively short (control response back to normal in 10–25 minutes). In the case of a compound with a longer duration of action, the control response would only return to normal over a severalfold longer period of time. We prefer the bronchodilator to be both β2 selective and long acting Specific bronchodilators which may be mentioned are 2-(tert-butylamino)-1-(4-hydroxy-3-hydroxymethyl-phenyl)-ethanol 1-(3,5-dihydroxyphenyl)-2-(tert-butylamino)-ethanol 1-(3,5-dihydroxyphenyl)-1-hydroxy-2-[(4-hydroxyphenyl)isopropylamino]ethane (3,4-dihydroxyphenyl)(piperid-2-yl)methanol

[5-(1-hydroxyethyl-2-t-butylamino)-2-hydroxyphenyl]urea 2-hydroxymethyl-3-hydroxy-6-(1-hydroxy-2-t-butylaminoethyl)pyridine 2,2'-hexamethylenedi-iminobis[1-(3,4-dihydroxyphenyl)-ethanol]

(±)-erythro-8-hydroxy-5-[1-hydroxy-2-(isopropylamino)-butyl]carbostyril

D,L-7-{3-[(β,3,5-trihydroxy-phenylethyl)amino]propyl}-1,3-dimethylxanthene

2'-hydroxy-5'-[1-hydroxy-2-(isopropylamino)ethyl]-methanesulphonanilide, and 1-(3-hydroxymethyl-4-hydroxy-phenyl)-1-hydroxy-2-[(4-methoxyphenyl)isopropylamino]ethane We particularly prefer the salt with 1-(3,5-dihydroxyphenyl)-1-hydroxy-2-[(4-hydroxyphenyl)isopropylamino]-ethane.

The salt may be of both the carboxylic acid groups of the 1,3-bis(2-carboxychromon-5-yloxy)propan-2-ol or of only one carboxylic acid group, the other carboxylic acid group either remaining free or being in the form of a salt with another pharmaceutically acceptable cation, e.g. sodium.

The salt may be made by a metathetical process, e.g. by reacting a suitable salt, such as the sodium salt, of 1,3-bis(2-carboxychromon-5-yloxy)propan-2-ol with an appropriate salt, e.g. the hydrochloride or sulphate, of the bronchodilator base. However the salt is preferably produced by reacting the free acid, 1,3-bis(2-carboxychromon-5-yloxy)propane-2-ol with the free bronchodilator base, as such a process does not produce a biproduct inorganic salt. The reaction may be carried out in a solvent which is inert under the reaction conditions. The solvent is preferably one in which the desired salt is soluble, e.g. water. The desired salt may be isolated and purified, for example, by crystallisation or by freeze drying.

According to the invention we therefore provide the salt when not in solution, e.g. the salt when in a substantially dry form, or when in admixture with insufficient liquid, e.g. water, to dissolve it all.

The salt may, if desired, be used in conjunction with one or more other salts of 1,3-bis(2-carboxychromon-5-yloxy)propan-2-ol, notably the disodium salt thereof.

According to our invention we also provide a pharmaceutical mixture comprising (a) one or more of 1,3-bis(2-carboxychromon-5-yloxy)-propan-2-ol, or a pharmaceutically acceptable salt thereof, (herein referred to collectively as 'active ingredient A') in combination with (b) one or more long acting or β2 selective bronchodilators, as hereinbefore defined, or a pharmaceutically acceptable salt thereof, e.g. the sulphate, the hydrochloride, the maleate etc. in solid form (herein collectively referred to as 'active ingredient B').

Solid compositions are advantageous to liquid or solution compositions, which latter are administered by nebuliser and which take a tediously long time to administer to the patient and require cumbersome apparatus which usually requires access to an external source of power, e.g. electricity.

We prefer to use the di-sodium salt of 1,3-bis(2-carboxychromone-5-yloxy)propan-2-ol, which is commonly known as sodium cromoglycate, or a salt with the bronchodilator as active ingredient A. We also prefer to use only one active ingredient A in admixture with one bronchodilator as active ingredient B.

The ratio of active ingredients A and B in the composition will vary with the particular active ingredients, and the specific purpose for which the composition is intended. When active ingredient A is itself a salt of 1,3-bis(2-carboxychromon-5-yloxy)propan-2-ol with a β2 selective bronchodilator it may be necessary to use, none, or only a very small proportion of 'free' bronchodilator base or of another salt thereof as active ingredient B.

A suitable dose of active ingredient A for inhalation is in the range 1 to 100 mg and preferably 1 to 20 mg, (measured as sodium cromoglycate).

A suitable dosage of active ingredient B for inhalation and a suitable number of parts by weight of active ingredient A (measured as sodium cromoglycate) to one part by weight of active ingredient B are specified below:

| Compound | Dose in micro g | Ratio (pressurised aerosol formulation) | Ratio (dry powder formulation) |
|---|---|---|---|
| 2-(tert-butylamino)-1-(4-hydroxy-3-hydroxymethylphenyl)-ethanol (as the sulphate) | 50 to 300, preferably 50 to 200 | 4 to 20 | 80 to 400 |
| 1-(3,5-dihydroxyphenyl)-2-(tert-butylamino)ethanol (as the sulphate) | 100 to 600 preferably 100 to 500 | 2 to 10 | 40 to 200 |
| 1-(3,5-dihydroxyphenyl)-1-hydroxy-2-[(4-hydroxyphenyl)-isopropylamino]ethane (as the hydrobromide) | 100 to 500 | 2 to 10 | 40 to 200 |
| (3,4-dihydroxyphenyl)(piperid-2-yl)methanol (as the hydrobromide) | 100 to 500 | 2 to 10 | 40 to 200 |
| [5-(1-hydroxyethyl-2-t-butyl-amino)-2-hydroxyphenyl]urea (as the hydrochloride) | 100 to 500 | 2 to 10 | 40 to 200 |
| 2-hydroxymethyl-3-hydroxy-6-(1-hydroxy-2-t-butylaminoethyl)-pyridine | 100 to 2000 | 2 to 40 | 40 to 800 |
| 2,2'-hexamethylenedi-iminobis-[1-(3,4-dihydroxyphenyl)ethanol] (as the dihydrochloride) | 100 to 500 | 2 to 10 | 40 to 200 |
| (±)-erythro-8-hydroxy-5-[1-hydroxy-2-(isopropylamino)butyl]-carbostyril (as the monohydrochloride) | 50 to 300 | 4 to 20 | 80 to 400 |
| D,L-7-{3-[(β,3,5-trihydroxy-phenylethyl)amino]propyl}-1,3-dimethylxanthene (as the hydrochloride) | 150 to 750 | 1.3 to 6.7 | 26.7 to 133.3 |
| 2'-hydroxy-5'-[1-hydroxy-2-(isopropylamino)ethyl]-methanesulphonanilide | 50 to 500 | 2 to 20 | 40 to 400 |
| 1-(3-hydroxymethyl-4-hydroxy-phenyl)-1-hydroxy-2-[(4-methoxyphenyl)isopropyl-amino]ethane | 50 to 500 | 2 to 20 | 40 to 400 |

It is much preferred that the dose of bronchodilator be such as to give a sustained rather than a transitory action.

The mixture may be administered as divided doses from 1 to 6, and preferably 2 to 4, times per day. Each dose may comprise one or more unit doses.

The specific ratios of particular active ingredients A and B in any composition according to the invention can vary over a wide range. However we prefer a composition containing from 0.4 to 400 parts by weight, and more preferably from 2 to 200 parts by weight of active ingredient A (measured as sodium cromoglycate) for each part by weight of active ingredient B. We particularly prefer a composition containing sodium cromoglycate and 1-(3,5-dihydroxyphenyl)-2-(t-butylamino)ethanol, or a pharmaceutically acceptable salt, e.g. the sulphate, thereof.

The mixtures according to the invention may be made by mixing together the various active ingredients using conventional techniques known per se.

The salts, mixtures and compositions of the invention are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Pat. No. 1,292,601). The salts and compositions have also been found to inhibit the degranulation of mast cells and to interfere with reflex pathways in experimental animals and man, in particular those reflexes associated with lung function. In man, both subjective and objective changes which result from the inhalation of specific antigen by sensitised subjects are inhibited by prior administration of the new salts and compositions. Thus the new salts and compositions are useful in the treatment of reversible airway obstruction and/or to prevent the secretion of excess mucous. They are thus useful for the treatment of allergic asthma, so-called 'intrinsic' asthma (in which no sensitivity to extrinsic antigen can be demonstrated), exercise etc. induced asthma, rhinitis, farmer's lung, bird fancier's disease, bronchitis, coughs (including whooping cough) and the nasal and bronchial obstructions associated with the common cold. The new salts and compositions are also of value in the treatment of other conditions in which antigen-antibody reactions or excess mucous secretion are responsible for, or are an adjunct to, disease.

The new salts or mixtures of the invention may be administered by a wide variety of routes and may act systemically or locally. Thus the compounds may be administered by oral or nasal inhalation to the lung, directly to the nose or eye, to the buccal cavity, oesophageally or to other available surfaces of the body. The new salts or mixtures may be administered directly to the organ or part of the body showing symptoms or to a part remote from that showing symptoms.

The new salts and mixtures of the invention may be used in a variety of dosing schedules, either on their own or in conjunction with one or more other active compounds.

The new salts of the invention, and the active components of the mixtures, may be prepared in a wide variety of sizes. Thus for inhalation and other uses the compounds may have a mass median diameter of from 0.01 to 10 microns, preferably from 2 to 6, and most preferably from 2 to 4, microns. Larger sized crystals or agglomerates, e.g. granules or hard pellets, of the compounds, which larger sized materials will tend to have higher bulk densities than the finely divided materials, may be used as intermediates in the formulation of the compounds, e.g. as tablets, or may be used on their own or for filling into capsules. The finely divided compounds may also be agglomerated into 'soft' pellets or granules which are sufficiently strong to be packed, e.g. encapsulated, by machines and to be transported, but are sufficiently weak to be broken up to produce fine particles when used in an inhalation device.

According to our invention we also provide a pharmaceutical composition comprising (preferably less than 80%, and more preferably less than 50% by weight of) a salt or mixture according to the invention, in admixture with a pharmaceutically acceptable adjuvant, diluent or carrier.

We particularly prefer the composition not to contain material capable of causing an adverse, e.g. an allergic, reaction in the patient. Materials which can cause adverse reactions are more fully described in Belgian Pat. No. 854,690.

For administration by inhalation the new salts or mixtures may be formulated with a compressed gas, e.g. nitrogen, or a liquified propellant as a pressurised aerosol composition, the composition preferably containing from 1 to 20% w/w of the active agent(s). The composition also preferably contains less than about 5% w/w of water and more preferably is substantially anhydrous.

The liquified propellant is preferably a gas at room temperature (20° C.) and atmospheric pressure (760 mm of mercury), and should also be non-toxic. Among the suitable liquified propellants which may be employed are alkanes containing up to five carbon atoms, e.g. butane or pentane, or a C 1 to 6 alkyl chloride, e.g. methyl, ethyl or propyl chlorides. The most suitable liquified propellants are the fluorinated and fluorochlorinated C 1 to 3 (preferably C 1 or 2) alkanes such as are sold under the Registered Trade Mark 'Freon'. The preferred halogenated alkanes may be represented generally by the formula $C_mH_nCl_yF_z$, wherein m is an integer less than 3, n is an interger or zero, y is an integer or zero, and z is an integer, such as $n+y+z=2 m+2$. Examples of these propellants are dichlorodifluoromethane (Propellant 12), 1,2-dichlorotetrafuoroethane (Propellant 114) $CClF_2.CClF_2$, trichloromonofluoromethane (Propellant 11), dichloromonofluoromethane (Propellant 21), monochlorodifluoromethane (Propellant 22), trichlorotrifluoroethane (Propellant 113), and monochlorotrifluoromethane (Propellant 13). Mixtures of the above propellants may be used to give improved vapour pressure characteristics, e.g. Propellant 11 with Propellant 12, or Propellant 12 with Propellant 114. We prefer compositions which do not contain Propellant 11. It is desirable that the vapour pressure of the propellant employed be between 3,500 and 4,550 grams per sq. cm. at 24° C.

The composition may also contain a surface active agent, e.g. a liquid or solid non-ionic surface active agent or a solid anionic surface active agent.

The preferred solid anionic surface active agent is sodium dioctyl-sulphosuccinate.

The amount of the surface active agent to be used is related to the solids content of the suspension and to the particle size of the solids.

When a liquid, non-ionic surface active agent is employed it should have an hydrophile-lipophile balance (HLB) ratio of less than 10 and preferably of from 1 to 5.

We prefer the surface active agent to comprise from 0.05 to 1.5% by weight of the total composition.

Suitable non-ionic surface active agents are phospholipids, e.g. endogenous phospholipids, the esters or partial esters of fatty acids containing from 6 to 22 carbon atoms, such as caproic, octoic, lauric, palmitic, stearic, linoleic, linolenic, oleostearic and oleic acids with an aliphatic polyhydric alcohol or its cyclic anhydride such as ethylene glycol, glycerol, erythritol, arabitol, mannitol, sorbitol, the hexitol anhydrides derived from sorbitol (the sorbitan esters sold under the Registered Trade Mark 'Spans') and the polyoxyethylene and polyoxypropylene derivatives of these esters. Mixed esters, such as mixed or natural glycerides may be employed. The preferred liquid non-ionic surface active agents are the oleates of sorbitan, e.g. those sold under the Registered Trade Marks 'Arlacel C' (Sorbitan sesquioleate), 'Span 80' (Sorbitan monooleate) and 'Span 85' (Sorbitan trioleate). Other suitable non-ionic surface active agents are sorbitan monolaurate, polyoxyethylene sorbitol tetraoleate, polyoxyethylene sorbitol pentaoleate, polyoxypropylene mannitol dioleate and lecithin.

For inhalation as a powder formulation the active agent(s) in finely divided form may be used in admixture with a larger sized carrier comprising particles, e.g. of up to 400 microns diameter. We prefer at least 90% by weight of the particles of the active agent(s) to have an effective particle size below 10 microns (and preferably of from 0.01 to 10 microns), and at least 90% by weight of the particles of the carrier to have an effective particle size below 400 microns, and at least 50% by weight of the particles of the carrier to have an effective particle size above 30 microns. Effective particle size for particles below 30 microns may be measured by a Coulter counter. Effective particle size for particles above 30 microns may be measured by an Alpine air jet sieve.

Desirably, at least 95% by weight of the particles of the active agent(s) have an effective particle size in the range 0.01 to 10 microns. Preferably at least 90%, and more desirably at least 95%, by weight thereof have an effective particle size in the range 0.1 to 10 microns. Suitably, at least 50% by weight of the particles of the active agent(s) have an effective particle size in the range 2 to 6 microns.

The particle size spectrum of the carrier will depend on the particular inhalation device from which the formulation is to be dispersed. It is however desirable to avoid carrier particles of less than 10 microns in size, thus minimising the number of non-drug particles which penetrate deep into the lung. A large proportion of very large particles may also cause a gritty feel in the mouth of the user and is therefore less preferred. Use of a carrier of large particle size may also cause problems in filling when using filling machines which involve a dosator which picks up powder by dipping into a powder bed from above. However, use of a carrier of large particle size may ease filling when using machines in which a die is filled from above, but may incline the composition to segregate during transport or storage. Thus, desirably, at least 95% by weight of the particles of carrier have an effective particle size below 400 microns. Preferably at least 50%, and more desirably at least 70%, by weight of the carrier particles have an effective particle size in the range 30 to 150, especially 30 to 80, microns.

The composition preferably contains from 20 to 80% by weight, more especially from 30 to 70% by weight, and particularly from 40 to 60% by weight of the total active agents, and from 80 to 20% by weight, more especially from 70 to 30% by weight and particularly from 60 to 40% by weight of the carrier.

The powder compositions may be prepared by mixing the ingredients together in one or, preferably, more (e.g. two) steps in a mixer, such as planetary or other stirred mixer.

The carrier may be any non-toxic material which is chemically inert to the compounds and is acceptable for inhalation or for administration to the nose. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose; polysaccharides, e.g. starches, dextrins or dextrans. A particularly preferred carrier is lactose, e.g. crystalline lactose.

The powder compositions will generally be put up in sealed gelatine, plastic or other capsules. The container is preferably loosely fitted to less than about 80% by volume, preferably less than about 50% by volume, with the powder composition.

Alternatively, for inhalation the new salts or mixtures may be used in pellet or granule form, wherein the pellet or granule is soft, is from 10 to 1,000, preferably 30 to 500 microns, in diameter and comprises an agglomeration of individual medicament particles, at least 90% by weight of which have a diameter of less than 10 microns.

The soft pellet or granule preferably has an internal coherence such that the pellet or granule remains intact when filled into a container, e.g. a capsule, using automatic or semi-automatic filling machines, under conditions of transport and storage, and when fluidised within a container in the device from which it is intended to dispense the pellets or granules and yet may be broken up into particles of a therapeutically effective size outside the container as it discharges from the container.

We have found that satisfactory soft pellets or granules for use in insufflators of the type described in British Pat. No. 1,182,779 (commercially available under the Registered Trade Mark 'Spinhaler') and powered by human inhalation have a mean size in the range of from 50 to 250 microns, preferably a mean size in the range 120 to 160 microns and most preferably a mean size of about 140 microns.

The invention is illustrated, but in no way limited by the following Examples.

EXAMPLE 1

Pressurised aerosol delivering sodium cromoglycate (1 mg) and 2-(tert-butylamino)-1-(4-hydroxy-3-hydroxymethylphenyl)ethanol sulphate (0.1 mg).

| | |
|---|---|
| Sodium cromoglycate (micronised, dried) | 1.4420 % w/w |
| 2-(tert-butylamino)-1-(4-hydroxy-3-hydroxy-methylphenyl)ethanol sulphate (micronised) | 0.1442 |
| Sorbitan trioleate | 1.0000 |
| Dichlorotetrafluoroethane | 38.9655 |
| Dichlorodifluoromethane | 58.4483 |

Cool the dichlorodifluoromethane to $-55°$ C. and disperse the sorbitan trioleate in it using a high-shear mixer. Disperse the sodium cromoglycate and the 2-(tert-butylamino)-1-(4-hydroxy-3-hydroxymethylphenyl)ethanol sulphate in the mix and add the dichlorotetrafluoroethane, previously cooled to $-55°$ C. Fill the suspension into cans, and crimp a metering valve of 50 $\mu$l capacity onto each can.

EXAMPLE 2

Pressurised aerosol delivering sodium cromoglycate (1 mg) and 1-(3,5-dihydroxyphenyl)-2-(tert-butylamino)-ethanol sulphate (0.25 mg).

| Sodium cromoglycate (micronised, dried) | 1.4286 % w/w |
|---|---|
| 1-(3,5-dihydroxyphenyl)-2-(tert-butyl-amino)ethanol sulphate (micronised) | 0.3571 |
| Sorbitan trioleate | 1.0000 |
| Trichlorofluoromethane | 24.3036 |
| Dichlorotetrafluoroethane | 24.3036 |
| Dichlorodifluoromethane | 48.6071 |

Dissolve the sorbitan trioleate in the trichlorofluoromethane and disperse the sodium cromoglycate and 1-(3,5-dihydroxyphenyl)-2-(tert-butylamino)ethanol sulphate in the solution. Cool the solution to −55° C. and add the dichlorotetrafluoroethane and dichlorodifluoromethane, cooled to −55° C. Fill the suspension into cans and crimp a metering valve of 50 µl capacity onto each can.

EXAMPLE 3

Pressurised aerosol delivering sodium cromoglycate (1 mg) and D,L-7-{3-[β,3,5-trihydroxyphenylethyl)amino]propyl}-1,3-dimethylxanthene hydrochloride (0.5 mg).

| Sodium cromoglycate (micronised, dried) | 1.4663 |
|---|---|
| D,L-7-{3-[β,3,5-trihydroxyphenylethyl)-amino]propyl}-1,3-dimethylxanthene hydrochloride (micronised) | 0.7331 |
| Sorbitan trioleate | 0.5000 |
| Trichlorofluoromethane | 10.0000 |
| Dichlorotetrafluoroethane | 13.0951 |
| Dichlorodifluoromethane | 74.2055 |

Prepare as in Example 2.

EXAMPLE 4

Dry powder formulation for inhalation containing in each cartridge sodium cromoglycate (20 mg anhydrous weight), 2-(tert-butylamino)-1-(4-hydroxy-3-hydroxymethylphenyl)ethanol sulphate (0.2 mg) and classified lactose.

| Sodium cromoglycate (8% water-micronised) | 50.0% w/w (as anhydrous material) |
|---|---|
| 2-(tert-butylamino)-1-(4-hydroxy-3-hydroxymethyl-phenyl)ethanol sulphate (micronised) | 0.5% w/w |
| Lactose (classified 30–80 microns) | q.s. ad 100% |

Mix the 2-(tert-butylamino)-1-(4-hydroxy-3-hydroxymethyl-phenyl)ethanol sulphate with the classified lactose by trituration and then mix with the sodium cromoglycate using a planetary mixer. Fill into No. 2 hard gelatin capsules, such that each capsule contains the desired amount of the active ingredients.

EXAMPLE 5

Dry powder formulation for inhalation containing in each cartridge the equivalent of 20 mg anhydrous sodium cromoglycate and 0.5 mg 1-(3,5-dihydroxyphenyl)-2-(tert-butylamino)ethanol sulphate in a classified lactose carrier.

| Sodium cromoglycate (8% water-micronised) | 50.0% w/w (as anhydrous material) |
|---|---|
| 1-(3,5-dihydroxyphenyl)-2-(tert-butylamino)ethanol sulphate (micronised) | 2.5% w/w |
| Classified lactose | q.s. ad 100.0% w/w |

Prepare as in Example 4.

EXAMPLE 6

Dry powder formulation for inhalation containing in each cartridge the equivalent of 20 mg anhydrous sodium cromoglycate and 0.5 mg 1-(3,5-dihydroxyphenyl)-1-hydroxy-2-[(4-hydroxyphenyl)isopropylamino]ethane hydrobromide in a classified lactose carrier.

| Sodium cromoglycate (8% water-micronised) | 50.0% w/w (as anhydrous material) |
|---|---|
| 1-(3,5-dihydroxyphenyl)-1-hydroxy-2-[(4-hydroxyphenyl)isopropyl-amino]ethane hydrobromide (micronised) | 2.5% w/w |
| Classified lactose | q.s. ad 100.0% w/w |

Prepare as in Example 4.

EXAMPLE 7

Soft pellet formulation for inhalation containing in each cartridge the equivalent of 20 mg anhydrous sodium cromoglycate and 0.1 mg 2-(tert-butylamino)-1-(4-hydroxy-3-hydroxymethylphenyl)ethanol sulphate.

| Sodium cromoglycate (micronised) | 99.51% w/w (as anhydrous material) |
|---|---|
| 2-(tert-butylamino)-1-(4-hydroxy-3-hydroxymethylphenyl)ethanol sulphate (micronised) | 0.49% w/w |

Expose the sodium cromoglycate to water vapour so as to bring the moisture content to between 9.5 and 10.5% w/w. Triturate the 2-(tert-butylamino)-1-(4-hydroxy-3-hydroxymethylphenyl)ethanol sulphate with one-tenth of the sodium cromoglycate and then mix with the remaining sodium cromoglycate in a drum roller for 15 minutes. Sieve the mixture through a 100 mesh screen, and roll the sieved powder in the drum roller for a further 15 minutes. Fill the product into No. 2 hard gelatin capsules so that each contains the desired amount of the active ingredients.

EXAMPLE 8

Soft pellet formulation for inhalation containing in each cartridge the equivalent of 20 mg anhydrous sodium cromoglycate and 0.25 mg 1-(3,5-dihydroxyphenyl)-2-(tert-butylamino)ethanol sulphate.

| Sodium cromoglycate (micronised) | 98.77% w/w (as anhydrous material) |
|---|---|
| 1-(3,5-dihydroxyphenyl)-2-(tert-butylamino)ethanol sulphate (micronised) | 1.23% w/w |

Prepare as in Example 7.

EXAMPLE 9

Soft pellet formulation for inhalation containing in each cartridge the equivalent of 20 mg anhydrous sodium cromoglycate and 0.25 mg (3,4-dihydroxyphenyl)(piperid-2-yl)methanol hydrobromide.

| | | |
|---|---|---|
| Sodium cromoglycate (micronised) | 98.77% w/w | (as anhydrous material) |
| (3,4-dihydroxyphenyl)(piperid-2-yl)methanol hydrobromide (micronised) | 1.25% w/w | |

Prepare as in Example 7.

EXAMPLE 9

Mono 1-(3,5-dihydroxyphenyl)-1-hydroxy-2-[(4-hydroxyphenyl)isopropylamino]ethane salt of 1,3-bis(2-carboxychromon-5-yloxypropan-2-ol 1-(3,5-dihydroxyphenyl)-1-hydroxy-2-[(4-hydroxyphenyl)isopropylamino]ethane (3.03 g) and cromoglycic acid (4.68 g) were dissolved in water (100 ml) with heating, then the solution was cooled and freeze-dried to afford the mono salt as an off-white powder.

Found: C 50.1; H 5.8; N 1.67% $C_{40}H_{37}NO_{15}.18.9\%$ $H_2O$ requires: C 50.47; H 6.04; N 1.47%

EXAMPLE A

Anaphylactic bronchoconstriction in rats passively sensitized with rat anti-conalbumin serum Materials and Methods 1. Preparation of antiserum for passive sensitization
Rats are sensitized as follows:
Day 0 Conalbumin (5 mg/kg) i.m. plus *B.pertussis* vaccine (0.5 ml/animal) i.p. Day 10 *N.brasiliensis* ($4 \times 10^3$ larvae). On day 24 or 25 the blood is collected by cardiac puncture and the antiserum separated and pooled.

2. Passive sensitization
Sprague Dawley rats are passively sensitized by i.v. injection of the antiserum as prepared above.

The potency of the antiserum will vary from batch to batch, therefore a preliminary experiment should be done, using groups of 3 rats dosed with 0.125 to 1.0 ml serum, to establish a dose which gives good sub-maximal bronchoconstriction.

3. Preparation of the animal for recording and measurement of anaphylactic bronchoconstriction.

18-24 hours are sensitization the rats are anaesthetized with pentobarbitone. The tail vein of the rat is cannulated using a needle inserted in narrow tubing to provide a flexible connection for i.v. dosing. Each animal is then prepared for the measurement of airway resistance. The trachea is cannulated and the animal ventilated, using a Starling minature respiration pump at a stroke volume of 3-5 ml and a rate of 72 strokes/min. Inflation pressure is kept constant at 9 cm water by means of a water valve, and the stroke volume is set, at the start of the experiment, so that one bubble of air overflows through the water valve at each inspiration. This overflow, i.e. air which does not enter the trachea, passes through a pneumotachograph tube connected to a differential air pressure trassducer (Grass PT5A) and a Devices recorder upon which changes in overflow are displayed. The increase in overflow, caused by antigen-induced bronchoconstriction which follows the injection of egg albumin 25 mg/kg i.v. is measured as a % of the maximal overflow (obtained by clamping off the tube leading to the trachea).

4. Effect of test compounds given intravenously
After taking a control record of normal respiration for 3 to 5 minutes a dose of test compound or an equivalent volume of saline is given i.v. 1 minute before a challenge dose of antigen (as above). The inhibitory effect of the test compound or mixture is determined by $$100 - \left( \frac{\% \text{ bronchoconstriction in test group}}{\% \text{ bronchoconstriction in control group}} \right) \times 100$$

We claim:
1. A pharmaceutical mixture comprising
   (a) a therapeutically effective amount of one or more of 1,3-bis(2-carboxychromon-5-yloxy)propan-2-ol, or a pharmaceutically acceptable salt thereof, as active ingredient A, in combination with
   (b) a therapeutically effective amount of one or more β2 selective bronchodilators, or a pharmaceutically acceptable salt thereof, in solid form, as active ingredient B.

2. A mixture according to claim 1, wherein active ingredient A is sodium cromoglycate.

3. A mixture according to claim 1 comprising from 0.4 to 400 parts by weight of active ingredient A, measured as sodium cromoglycate, for each part by weight of active ingredient B.

4. A mixture according to claim 3 comprising from 2 to 200 parts by weight of active ingredient A, measured as sodium cromoglycate, for each part by weight of active ingredient B.

5. A mixture according to claim 3 comprising from 4 to 400 parts by weight of active ingredient A, measured as sodium cromoglycate, for each part by weight of 2-(tert-butylamino)-1-(4-hydroxy-3-hydroxymethylphenyl)ethanol sulphate as active ingredient B.

6. A mixture according to claim 3 comprising from 2 to 200 parts by weight of active ingredient A, measured as sodium cromoglycate, for each part by weight of 1-(3,5-dihydroxyphenyl)-2-(tert-butylamino)ethanol sulphate as active ingredient B.

7. A mixture according to claim 3 comprising from 2 to 200 parts by weight of active ingredient A, measured as sodium cromoglycate, for each part by weight of 1-(3,5-dihydroxyphenyl)-1-hydroxy-2-[(4-hydroxyphenyl)isopropylamino]ethane hydrobromide as active ingredient B.

8. A mixture according to claim 3 comprising from 1.3 to 133.3 parts by weight of active ingredient A, measured as sodium cromoglycate, for each part by weight of D,L-7-{3-[(β,3,5-trihydroxyphenylethyl)amino]propyl}-1,3-dimethylxanthene hydrochloride as active ingredient B.

9. A pharmaceutical composition comprising a mixture according to claim 1 in admixture with a pharmaceutically acceptable adjuvant, diluent or carrier, and in a form suitable for inhalation.

10. A composition according to claim 9 in the form of a pressurised aerosol composition containing from 1 to 20% w/w of the active agents and comprising from 0.05 to 1.5% by weight of a surface active agent.

11. A composition according to claim 9 which is a powder formulation comprising the active agents in finely divided form in admixture with a coarse carrier, at least 90% by weight of the particles of the active agents having an effective particle size of below 10 microns, and at least 90% by weight of the particles of the carrier having an effective particle size below 400 microns, and at least 50% by weight of the particles of the carrier having an effective particle size above 30 microns.

12. A composition according to claim 9, in which the mixture is in pellet or granule form, wherein the pellet or granule is soft, is from 30 to 500 microns in diameter and comprises an agglomeration of individual medicament particles, at least 90% by weight of which have a diameter of less than 10 microns.

* * * * *